United States Patent
Collins, Sr. et al.

(10) Patent No.: US 8,663,993 B2
(45) Date of Patent: Mar. 4, 2014

(54) AUTOMATED PROTEIN ANALYZER

(75) Inventors: Michael J Collins, Sr., Charlotte, NC (US); Joseph J Lambert, Charlotte, NC (US); Timothy A Zawatsky, Charlotte, NC (US); David L Herman, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 420 days.

(21) Appl. No.: 12/721,688

(22) Filed: Mar. 11, 2010

(65) Prior Publication Data

US 2010/0291686 A1  Nov. 18, 2010

Related U.S. Application Data

(62) Division of application No. 11/846,598, filed on Aug. 29, 2007, now Pat. No. 8,147,759.

(51) Int. Cl.
*G01N 33/00* (2006.01)

(52) U.S. Cl.
USPC .............. 436/86; 436/164; 436/166; 436/174

(58) Field of Classification Search
USPC ........ 436/86, 164, 166, 174; 422/68.1, 82.05, 422/82.09, 513; 426/231
See application file for complete search history.

(56) References Cited

U.S. PATENT DOCUMENTS

| | | | |
|---|---|---|---|
| 3,061,280 A | | 10/1962 | Kraft et al. |
| 3,936,271 A | | 2/1976 | Statter |
| 3,985,032 A | | 10/1976 | Avakian |
| 4,135,816 A | | 1/1979 | Niemann et al. |
| 4,141,954 A | | 2/1979 | Shigetomi |
| 4,782,046 A | | 11/1988 | Brown et al. |
| 4,861,556 A | | 8/1989 | Neas et al. |
| 4,865,992 A | | 9/1989 | Hach et al. |
| 4,882,286 A | | 11/1989 | Neas et al. |
| 4,946,797 A | | 8/1990 | Neas et al. |
| 5,038,775 A | | 8/1991 | Maruscak et al. |
| 5,114,679 A | * | 5/1992 | Reifler et al. ................. 422/513 |
| 5,156,809 A | | 10/1992 | Hupe et al. |
| 5,447,838 A | | 9/1995 | Meiklejohn et al. |
| 5,861,317 A | | 1/1999 | Tanihata |
| 5,866,804 A | | 2/1999 | O'Keeffe |
| 5,958,714 A | | 9/1999 | Gordon et al. |
| 5,996,811 A | | 12/1999 | Kitajima et al. |
| 6,404,500 B1 | * | 6/2002 | Schneider et al. ............ 356/432 |
| 6,866,820 B1 | | 3/2005 | Otto et al. |
| 7,130,752 B2 | | 10/2006 | Yoshida et al. |
| 2002/0048215 A1 | | 4/2002 | McGill |
| 2002/0169518 A1 | | 11/2002 | Luoma, II et al. |
| 2002/0197631 A1 | | 12/2002 | Lawrence et al. |
| 2003/0086823 A1 | | 5/2003 | Fernando et al. |
| 2005/0245492 A1 | | 11/2005 | Lephart et al. |
| 2007/0092404 A1 | | 4/2007 | Hughes |
| 2009/0087917 A1 | | 4/2009 | Collins et al. |

FOREIGN PATENT DOCUMENTS

| | | |
|---|---|---|
| EP | 0 455 923 | 11/1991 |
| FR | 2735400 | 12/1996 |
| GB | 934 304 A | 8/1963 |
| JP | 61-54245 | 3/1986 |
| JP | 03-292874 | 12/1991 |
| JP | 09-243635 | 9/1997 |
| JP | 11-201973 | 7/1999 |
| JP | 11-304803 | 11/1999 |
| JP | 2003-270250 | 9/2003 |
| WO | 2005/063962 A | 7/2005 |

OTHER PUBLICATIONS

De la Camp, Ulrich et al. "Proper Use of Volumetric Glassware." Web site. <http://replay.waybackmachine.org/20030120062700/http://www.csudh.edu/oliver/che230/labmanual/volglas.htm>, accessed by the examiner on Apr. 7, 2011, archived by the Internet Archive on Dec. 6, 2003.*

"Weighing Objects Tutorial." Web site. <http://replay.waybackmachine.org/20061213014054/http://www.chem.ubc.ca/courseware/121/tutorials/exp1A/weigh/>, accessed by the examiner on Apr. 7, 2011, archived by the Internet Archive on Dec. 13, 2006.*

McGown, Evelyn, "UV Absorbance Measurements in SpectraMax Microplate Spectrophotometers MaxLine Application Note #32", 1999, Biocompare website <http.//www.biocompare.com/Articles/ApplicationNote/1433/UV-Absorbance-Measurements-In-SpectraMax-Microplate-Spectrophotometers-MaxLine-Application-Note-32.html>; accessed Dec. 17, 2010.

(Continued)

*Primary Examiner* — Christopher A Hixson

(57) ABSTRACT

A dye binding method for protein analysis is disclosed. The method includes the steps of preparing an initial reference dye solution of unknown concentration from an initial reference dye concentrate and creating an electronic signal based upon the absorbance of the initial reference dye solution. Thereafter, an electronic signal is created based upon the absorbance of a dye filtrate solution prepared from the initial reference dye solution and an initial protein sample. The absorbance signals from the reference dye solution and the dye filtrate solution are sent to a processor that compares the respective absorbances and calculates the protein content of the protein sample based upon the difference between the absorbances. An electronic signal is created based upon the absorbance of a successive dye filtrate solution prepared from the reference dye solution and a successive protein sample, and the absorbance signal from the successive sample dye filtrate solution is sent to the processor to calculate the protein content of the successive sample based upon the difference between the absorbance of the initial reference dye solution and the absorbance of the successive dye filtrate solution.

15 Claims, 9 Drawing Sheets

(56) References Cited

OTHER PUBLICATIONS

Skehel, J. Mark, "Preparation of Extracts from Animal Tissues" from Methods in Molecular Biology, vol. 244, Protein Purification Protocols, 2nd ed. (2004).

Udy; "A Rapid Method for Estimating Total Protein in Milk," Nature, vol. 178, pp. 314-315, Aug. 11, 1956.

Seperich et al, "Dye Binding Procedure for the Estimation of Protein Content of Meat Components and Sausage Emulsions," Journal of Food Science, vol. 44 (1979), pp. 643-645.

FPM Product Data, "Combined Automatic Milk Fat and Protein Test with Digital Read-out," A/S N. Foss Electric, Date Unknown, 10 pages.

Pro-Milk MK II, Foss America, Inc., brochure, Nov. 22, 1971, pp. 1-6.

Udy Protein System, Seedburo Equipment Co. brochure, Feb. 24, 2006, pp. 1-2.

Analytical Techniques in Aquaculture Research, Accessed at http://www.aquaculture.ugent.be/ATA/analysis/prot_tot.htm, Mar. 2, 2006, pp. 1-5.

Udy, "Improved Dye Method for Estimating Protein,", J. Am. Oil Chemists' Soc., vol. 48, Jan. 1971, pp. 29A-33A.

Udy Protein Systems, accessed at http://www.udyone.com/prosysinfo.htm, accessed Nov. 30, 2005, pp. 1-4.

Udy Corporation, "Principles of Protein Measurement," accessed at: http://www.udyone.com/udydocs/udysys2.shtml, accessed May 7, 2007, pp. 1-5.

European Search Report of foreign counterpart application No. EP 08 16 3213 dated Oct. 2, 2009.

Nerac Dye-Binding Research Report No. 09537489-1.

Bio-Rad Protein Assy instruction manual, created Aug. 31, 1998, modified Mar. 18, 1999, Bulletin 9004, downloaded from www.biorad.com on Jun. 13, 2009, 27 pgs.

International Search Report of foreign counterpart application No. PCT/US08/74745 mailed Jul. 10, 2009, 1 pg.

European Search Report of foreign counterpart European Patent Application No. EP08171715 mailed Mar. 3, 2009, 2 pgs.

Papas, Andrew et al., "Evaluation of Robot Automated Drug Dissolution Measurements," Analytical Chemistry; 1985, vol. 57, No. 7; pp. 1408-1011.

Klunk et al.; Quantitative Evaluation of Congo Red Binding to Amyloid-like Proteins with a Beta-pleated Sheet Conformation; The Journal of Histochemistry and Cytochemistry, 1989, vol. 37, No. 8, pp. 1273-1281.

* cited by examiner

AUTOMATED PROTEIN ANALYZER

RELATED APPLICATIONS

This is a divisional of Ser. No. 11/846,598 filed Aug. 29, 2007.

BACKGROUND

The present invention relates to the determination of proteins in materials and particularly the protein content in various food samples.

Proteins are long chain molecules formed from the 20 basic amino acids and are the building blocks of all living systems. Proteins also represent, along with carbohydrates, fats and oils, a required food source for almost all living things.

Because proteins are a required food source, they are widely available in commercially available food products. Human beings tend to take protein in the form of meat, poultry, eggs seafood, dairy products, and nuts. Proteins are also a necessary part of many animal diets, including farm animals raised commercially. Protein sources for such animal feeds can also include meat, poultry, eggs, fish, and grains such as corn and oats.

Because so much human and animal food moves through a fairly sophisticated growing and distribution system, the knowledge of the amount of protein in food products is a valuable or even necessary for quality control, manufacture, storage, distribution, and use. As a result, the need to measure the protein content of various food products for both human and animal consumption has long existed.

One original (although indirect) test for protein content is the Kjeldahl test for nitrogen. In this test a protein sample is mixed with digestion ingredients (e.g., concentrated sulfuric acid, $H_2SO_4$) and often in the presence of mercuric oxide catalyst, potassium sulfate, and hydrogen peroxide. The acid converts the nitrogen into ammonium sulfate. The resulting solution is then made alkaline, liberating ammonia. The amount of ammonia can then be determined by titration with standard acid or any other relevant technique. A microwave instrument and technique for Kjeldahl analysis is set forth in commonly assigned U.S. Pat. No. 4,882,286.

Although the Kjeldahl test offers the advantage of determining protein content, it does so based on total nitrogen rather than protein per se. Thus, any given test results can include nitrogen from sources other than proteins, peptides, or amino acids. The Kjeldahl test also requires heating the sulfuric acid to temperatures that can reach 300° C. and in the presence of a metal catalyst. The Kjeldahl test is relatively complex, can take as long as 4 or 5 hours and can be susceptible to false nitrogen results. In the latter circumstance, confirmation requires at least a second test.

The Dumas technique presents an alternative analysis for total nitrogen and total carbon analysis. This is a combustion technique based upon the generation of gas phase products by extremely rapid combustion of the sample material. In an exemplary technique, a sample is carried in a tin combustion capsule and dropped into a combustion chamber that includes a catalyst and that is maintained at a relatively high temperature (1200° C.). A pulse of pure oxygen is admitted with the sample and the thermal energy from the resulting combustion of oxygen and tin generates an instantaneous temperature of as high as 1700° C. The heat produces total combustion of the relevant materials and the resulting gas phase products are collected in a stream of inert gas such as helium. Alternatively, the sample can be oxidized in the presence of a hot metal oxide. Carbon in the sample is converted to carbon dioxide ($CO_2$). The nitrogen combustion products include diatomic nitrogen ($N_2$) and the various oxides of nitrogen. These are directed through a reduction column, typically using heated metallic copper, to reduce the nitrogen oxides to diatomic nitrogen. The nitrogen can be determined from the volume of $N_2$ produced or by other comparative techniques such as thermal conductivity measurements.

The Dumas technique is limited to relatively small sample sizes (e.g. 0.5 grams or less) and like the Kjeldahl technique it is indirect because it measures total nitrogen rather than protein per se. The small sample size also makes the Dumas test less suitable for more heterogeneous materials.

Indirect techniques such as infrared or near infrared spectroscopy can be used but require relatively extensive calibration. Additionally, the presence of water tends to obscure the infrared absorption across a relatively wide portion of the spectrum. Because plant and animal proteins are so often found in the presence of at least some water, these infrared techniques are often inefficient.

For these and other reasons, proteins are sometimes measured by a dye-binding method, an original version of which was developed by Doyle Udy; e.g., "A Rapid Method for Estimating Total Protein in Milk," Nature, Vol. 178, pp 314-315, Aug. 11, 1956.

In a simplified description, a protein sample, usually in liquid suspension, is mixed at an appropriate pH with an aqueous solution of a dye molecule that will bind to the proteins. The solution contains an excess of the dye based upon the expected protein content of the sample. Proteins and these specified dyes react to form precipitated solids that remove the dye molecules from the solution. The solution is then filtered from the precipitate. The loss of color in the filtrate as measured in a spectrometer or colorimeter is proportional to the amount of dye (and thus protein) that formed the precipitate. This can also be expressed as the filtrate color being inversely proportional to the protein concentration (i.e., the higher the protein concentration the less color in the filtrate). As a typical example, a solution containing acid orange 12 dye (crocein orange G) has a readily identified broad absorption peak at about 482 nanometers (nm) and its absorbance follows Beer's Law.

As one advantage of this technique, the dye binds strongly with proteins (amino acids) rather than other nitrogen-containing compounds. Thus, it measures protein content more directly than do the nitrogen content techniques.

The technique does, however, require relatively complex measurement and handling techniques, or at least a plurality of manipulative steps each of which must be carried out properly in order to get an accurate result. For example, the user must prepare samples carefully because the small portions tested often represent much larger selections (potentially tons) of non-uniform materials. The test is generally carried out on suspensions which must be handled and stored and prepared appropriately. When solid materials are tested, they must typically be ground or pulverized to obtain an appropriate sample. Semi-solid materials tend to vary in their uniformity with some being almost homogeneous and others being quite non-homogeneous. When samples cannot be used immediately, preserving them for longer periods of time requires significant care.

The reagents present additional challenges and must be carefully handled in preparation, storage, and use. The accuracy requirements of solution preparation are relatively stringent and the preparations must be carried out appropriately.

In conventional practice, mixing an insoluble protein sample directly with a dye binding solution produces a heterogeneous mixture of the original sample, the dye-protein precipitate, and the remaining dye solution. This mixture is typically full of solids both from the dye binding reaction and the original sample and is generally too unwieldy for the necessary filtration and colorimetry steps. As a result, conventional dye-binding techniques tend to avoid directly mixing the dye solution and the protein sample (typically a food product). Instead—and in an additional step—a carefully weighed sample of protein is first diluted in measured fashion to about 10 times its original volume typically with water, or water, methanol and citric acid (citation). This diluted mixture is then blended to form a more homogenous diluted sample. The homogenized diluted sample is then mixed with the dye binding solution to initiate the dye-binding reaction.

As result, the necessary dilution introduces an additional manipulative step, an additional measurement step, and an additional calculation into the overall process.

Protein testing usually involves obtaining and preparing several different sets of the acid orange 12 dye. For example, in the basic Udy technique (Udy Corporation, *Principles of Protein Measurement*, http://www.udyone.com/udydocs/udysys2.shtml, accessed May 7, 2007) the filtrate color is measured using a digital colorimeter. The colorimeter is set using a reagent dye solution and a working reference dye solution. The standard reference dye solution is used to verify the proper concentration of the reagent dye solution and of the working reference dye solution. The reagent dye solution and the standard reference dye solutions are available in prepared format or as concentrates which can be diluted with distilled water and acetic acid before use. The user prepares a working reference dye solution from the reagent dye solution.

Stated more simply, the amount of protein in a given sample is measured by comparing the "before and after" color of the dye solution. Because the "before" color of any given solution can vary slightly depending upon its preparation, the colorimeter must be calibrated to match the individual dye solution before every test or before a series of tests that use that dye solution.

These relatively strict requirements produce good results, but the many steps involved compound the normally expected experimental uncertainty and each step also introduces the potential for outright error.

For example, typical dye binding protein sampling kits include a blender, a separate container and valves for the dye solution, a separate filter for separating the protein-dye precipitate from the filtrate, and a separate colorimeter. In the same manner, the "basic steps" of protein determination of meat products include the initial dilution step, then homogenizing the diluted sample in the blender, removing the sample from the blender with a syringe, a pipette, or by pouring it into a bottle; adding and measuring the reagent dye solution to the sample; shaking the sample; and filtering the reaction product into the colorimeter to read the absorbance, or in some cases a software-generated protein content based upon the absorbance (Udy Corporation, *Udy Protein Systems*, www.udyone.com/prosysinfo.htm, accessed Aug. 7, 2007).

These testing steps must be preceded by similarly strict steps for preparing standardized dye solutions for both reference (calibration) and testing purposes.

In the 1970's Foss (a/k/a Foss America, Foss Electric and Foss North America) offered a dye-binding test for milk in the form of the "Pro-Milk II" system. More recently, however, Foss has developed and offered automated devices that use either Kjeldahl techniques or infrared spectroscopy to measure protein content in milk products; e.g., Foss North America, Products direct, (online) http://www.foss.us/solutions/productsdirect.aspx (accessed July 2007).

Accordingly, a need exists for protein measurement techniques that minimize or eliminate these disadvantages.

SUMMARY

In one aspect the invention is a direct rapid automated protein analyzer. In this aspect the invention includes a homogenizer for reducing protein samples to small particles, a reaction vessel in material transfer communication with the homogenizer, a reservoir for binding dye composition in fluid communication with the reaction vessel, a metering pump between the reaction vessel and the reservoir for distributing discrete predetermined amounts of a binding dye composition to the reaction vessel, a filter in fluid communication with the reaction vessel for separating solids from filtrate after a dye binding reaction has taken place in the reaction vessel, and a colorimeter in fluid communication with the filter and the reaction vessel for measuring the absorbance of the filtrate from the reaction vessel and the filter.

In another aspect the invention is a dye binding method for protein analysis. The method includes the steps of preparing an initial reference dye solution of unknown concentration from an initial reference dye concentrate, creating an electronic signal based upon the absorbance of the initial reference dye solution, thereafter creating an electronic signal based upon the absorbance of a dye filtrate solution prepared from the initial reference dye solution and an initial protein sample, sending the absorbance signals from the reference dye solution and the dye filtrate solution to a processor that compares the respective absorbances and calculates the protein content of the protein sample based upon the difference between the absorbances, creating an electronic signal based upon the absorbance of a successive dye filtrate solution prepared from the reference dye solution and a successive protein sample, and sending the absorbance signal from the successive sample dye filtrate solution to the processor to calculate the protein content of the successive sample based upon the difference between the absorbance of the initial reference dye solution and the absorbance of the successive dye filtrate solution.

In yet another aspect, the invention is an automated protein analyzer that includes a reservoir for protein binding dye compositions, a protein-dye reaction vessel in fluid communication with the dye reservoir, a colorimeter in fluid communication with the reservoir, a pump in fluid communication with the reservoir and at least one of the colorimeter and the reaction vessel for transferring dye compositions from the reservoir to at least one of the colorimeter and the reaction vessel, a processor in signal communication with the colorimeter for receiving the absorbance output from the colorimeter, and memory in signal communication with the processor for storing output from the colorimeter that includes absorbance. The processor can compare the baseline absorbance of a reference binding dye composition to the specific absorbance of a binding dye composition following reaction with a protein to thereby calculate and determine the amount of protein in a protein sample based upon the difference between the absorbance of the reference dye and the absorbance of the reference dye after it has reacted with a protein sample.

In yet another aspect the invention is a method of calibrating a colorimeter for protein analysis and for analyzing a plurality of proteins samples. In this aspect, the method includes the steps of preparing an initial reference dye solution of unknown concentration from an initial reference dye concentrate and an approximate amount of fluid, forwarding the initial reference dye solution to a colorimeter and measuring the absorbency of the reference dye solution, thereafter forwarding an initial dye filtrate solution prepared from the reaction of the initial reference dye solution and a protein sample to the colorimeter and measuring the absorbency of the initial dye filtrate solution, sending the absorbance results from the initial dye filtrate solution and the initial reference dye solution to a processor that compares the respective absorbance and calculates the protein content of the sample based upon the difference between the absorbances, forwarding a successive dye filtrate solution to the colorimeter and measuring the absorbency of the successive dye filtrate solution, and sending the absorbance results from the successive dye filtrate solution to the processor to calculate the protein content of the successive sample based upon the difference between the absorbance of the initial reference dye solution and the absorbance of the successive dye filtrate solution.

In another aspect, the invention is an improvement in the dye binding method of protein analysis that includes the steps of mixing and homogenizing a non-homogeneous, insoluble protein sample directly with a dye-binding solution, drawing and filtering the remaining unreacted dye solution directly from the homogenized mixture of protein sample and dye-binding solution, and measuring the absorbance of the filtrate.

In another aspect, the invention is a protein analysis kit that includes a sample cup for mixing a protein sample with a dye-binding solution and a filter holder for being positioned in the sample cup. The filter holder includes a filter media and a depending spout below the filter media that reaches bottom portions of the cup when the filter media is positioned above the cup.

In yet another aspect, the invention is a protein analysis method that includes the steps of mixing a binding dye composition with a protein sample, attaching a filter to a colorimeter, pumping unreacted dye composition from the mixture, through the filter and to the colorimeter while the filter is attached to the colorimeter, and measuring the absorbance of the filtered dye composition in the colorimeter.

The foregoing and other objects and advantages of the invention and the manner in which the same are accomplished will become clearer based on the followed detailed description taken in conjunction with the accompanying drawings.

DETAILED DESCRIPTION

The present invention is an instrument and associated method for direct and rapid dye binding protein analysis. The terminology used in this specification and the claims is generally clear in context. As a helpful summary, however, some common terms are used in the following manner.

The term "reference dye concentrate" refers to a pre-prepared (typically commercially prepared) concentrated solution of a reference dye that will bind with a protein to form a protein-dye precipitate.

In use, a reference dye concentrate is mixed with an appropriate amount of water (and potentially other items as described later herein) to form a reference dye solution. In the protein analysis testing, the reference dye solution is mixed with a protein sample.

The term "initial reference dye concentrate" refers to a reference dye concentrate that is used to prepare an initial reference dye solution. In turn, the initial reference dye solution is used in the first of a series of protein analysis tests. The term "successive reference dye concentrate" refers to a second or further dye concentrate that is used to prepare a second or further reference dye solution. The successive reference dye solution is used in additional protein analysis tests. The initial dye reference concentrate and the successive reference dye concentrate can be the same dye.

The term "initial protein sample" refers to the earliest in a given series of protein samples that are tested according to the method. In the same manner, the term "successive protein sample" refers to a second or further member of a series of protein samples that are tested according to the method.

The term "dye filtrate solution" refers to the solution that remains after a protein sample has reacted with a reference dye solution. In turn, the "initial dye filtrate solution" represents the filtrate obtained after a first of several (or many) reactions between a protein sample and a reference dye solution. In the same manner, the term "successive dye filtrate solution" refers to the filtrate obtained after the second or further of several (or many) reactions between a protein sample and a reference dye solution.

Figure 1:
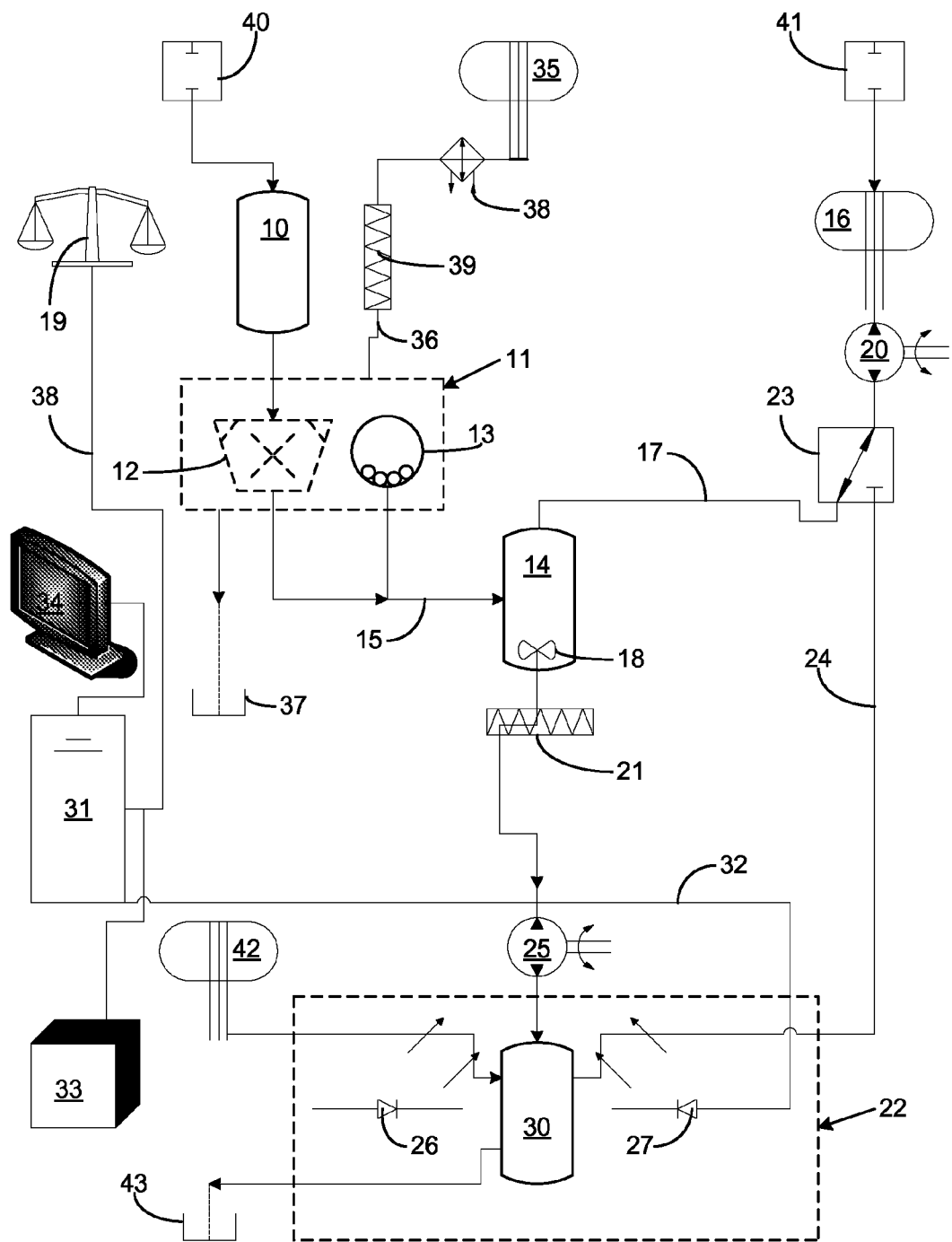
FIG. 1 is a schematic diagram of an instrument according to the present invention.

FIG. 1 is a schematic diagram of the elements of the instrument according to the invention. It will be understood that FIG. 1 illustrates the main functional elements of the instrument and that alternative arrangements of these elements can still fall within the scope of the invention and of the claims. FIG. 1 illustrates a sample holder or cup 10 which, as will be discussed with respect to the method aspects of the invention can be weighed (tared) prior to adding a protein sample. FIG. 1 illustrates a balance 19 for this purpose. The instrument transfers the sample from the cup 10 to a homogenizer broadly designated at 11. The homogenizer reduces the protein sample to particles that are as small as possible to thereby provide for a complete reaction with the binding dye. Accordingly, FIG. 1 schematically illustrates the homogenizer 11 as including a blender 12 or a ball mill 13. These are exemplary, however, and the homogenizer is not limited to these specific types of equipment.

A reaction vessel 14 is in material transfer communication with the homogenizer 11 as indicated by the line 15. As illustrated and described with respect to FIGS. 7-13, the functions of the cup 10 and the reaction vessel 14 can also be carried out using a single vessel by using a homogenizer 11 that can be inserted into the cup 10 and then removed on command. A reservoir 16 for the binding dye composition is in fluid communication with the reaction vessel 14 through the line 17. A metering pump 20 is positioned between the reaction vessel 14 and the reservoir 16 for distributing discrete predetermined (premeasured) amounts of the binding dye composition to the reaction vessel 14. In order to help drive the protein-dye reaction to completion, the instrument can include an appropriate agitator, shown as the stirrer 18 in FIG. 1.

A filter 21 is in fluid communication with the reaction vessel 14 for separating solids from filtrate after a dye binding reaction has taken place in the reaction vessel 14. A colorimeter broadly designated at 22 is in fluid communication with the filter 21 and the reaction vessel 14 for measuring the absorbance of the filtrate from the reaction vessel 14 that passes through the filter 21.

FIG. 1 also illustrates a valve 23 between the reservoir 16 and the reaction vessel 14 as well as a fluid line 24 between the valve 23 and the colorimeter 22. The combination of the valve 23 and the fluid line 24 permit binding dye solution from the reservoir to be directed to the reaction vessel 14 or directly to the colorimeter 22. This provides the instrument with the capacity to automatically make the reference measurements described in more detail with respect to the method aspects of the invention.

The illustrated embodiment also includes an optics pump 25 between the reaction vessel 14 and the colorimeter 22 for transferring filtrate from the reaction vessel to the colorimeter 22.

The nature and operation of a colorimeter is generally well understood in this art and will not be described in detail other than to schematically note as in FIG. 1 that the colorimeter 22 includes a light source shown as the diode 26, a photodetector shown as another diode 27, and a vessel 30 (often referred to as a cuvette) between the source and photodetector. The filtrate sample being measured is placed in the cuvette 30. FIG. 1 illustrates the cuvette 30 as a discrete vessel, but it will be understood that it could also include a portion of tubing or a small reservoir or any other appropriate functional item, provided it has the required transparency (minimal absorbency) in the color regions measured by the colorimeter. For example, in the embodiments illustrated in FIGS. 7-13 the optics are positioned above the vessel 14 and the optics pump 25 draws filtrate from the cup 10 and the filter 21 up into the colorimeter 22.

As well understood with respect to protein dye reactions, the absorbance of the filtrate follows Beer's Law, so that the measured color will be proportional to the concentration of dye in the filtrate sample. For the same reason, the source 26 is selected to emit light in the frequencies (color) that the filtrate will absorb and the detector 27 is likewise sensitive to the relevant frequencies. As noted earlier, Orange 12 dye has a characteristic absorption peak at about 482 nm.

In brief summary, Beer's Law states that the absorbance of a solution varies linearly with both the cell path length and the filtrate concentration according to the formula A=e l c, where "e" represents the molar absorptivity (sometimes referred to as the extinction coefficient), "l" represents the cell path length and "c" represents the concentration. The molar absorptivity varies with the wavelength of light used in the measurement.

A processor 31 is in signal communication with the colorimeter 22 through the line 32 which can represent a wire, a circuit board, or any other appropriate means of transmitting the data from the colorimeter 22 to the processor 31. The processor 31, which typically has the capabilities of a personal computer, includes appropriate memory schematically illustrated 33. Together, the processor 31 and the memory 33 store the absorbance results from both reference and sample tests, compare the absorbance of the reference and sample tests, and calculate the protein content of samples based on the comparisons. Because the protein content is based upon weight, the processor is also linked to the scale 19 through the line 38. 55. The use of processors and related electronic circuits to control instruments based on selected measured parameters (e.g. temperature and pressure) is generally well understood in this and related arts. Exemplary (but not limiting) discussions include Dorf, *The Electrical Engineering Handbook*, Second Ed. (1997) CRC Press LLC.

A display 34 is in communication with the processor through the line 35 which again can be part of an integrated circuit as well as a conventional wire or similar electronic connection. The display can be used in any conventional manner with the processor 31, and in the instrument according to the invention has the capacity to display items such as the absorbance of a particular sample in the colorimeter 22 and the protein content of a sample analyzed by the instrument. Although illustrated as a display, the instrument can include other forms of output including a printer, or digital output to memory, or another device. The display is, however, most typical for bench top use. The instrument can, of course, concurrently support a plurality of output formats.

FIG. 1 also illustrates some additional features that are included in exemplary embodiments of the instrument. A wash reservoir 35 is in fluid communication with the homogenizer 11 through the line 36 for providing the homogenizer with a washing fluid, typically either de-ionized water or a washing solution or sequential combinations of washing solutions and de-ionized water. It will be understood, of course, that more than one reservoir can be used for cleaning purposes. In some embodiments a heater 38 and filter 39 can be positioned between the wash reservoir 35 and the homogenizer 11. In turn, the homogenizer 11 is connected to a waste schematically illustrated at 37 which can be a drain or container or any other appropriate item. In the same manner, a wash reservoir 42 can be in communication with the colorimeter 22, and in particular the cuvette (or equivalent) 30 for cleaning the cuvette 30 between sample measurements. A corresponding waste 43 is likewise in communication with the cuvette 30 for completing a washing cycle. Depending upon the desired design for fluid flow, a common wash reservoir can be included in place of the separate reservoirs 35 and 42.

FIG. 1 also illustrates ports or openings 40 and 41 respectively that are provided to permit either the protein sample or cup 10 to be inserted into the device or in order to facilitate adding water or dye concentrate to the reservoir 16.

In another embodiment, the automated protein analyzer is a combination of (and with fluid communication between and among) the reservoir 16 for the dye binding composition, the protein dye reaction vessel 14, the colorimeter 22, and the pump 20 which is in fluid communication with the reservoir 16 and at least one of the calorimeter 22 and the reaction vessel 14 (and preferably both) for transferring dye compositions from the reservoir 16 to at least one of the colorimeter 22 or the reaction vessel 14. The processor 31 is in signal communication with the colorimeter 22 for receiving the absorbance output from the calorimeter 22 and the memory 33 is in signal communication with the processor 31 for storing output from the colorimeter that includes (but is not limited to) absorbance.

In this embodiment, the processor can compare the baseline absorbance of a reference binding dye composition to the specific absorbance of a dye filtrate solution following reaction with a protein to thereby calculate and determine the amount of protein in the protein sample based upon the difference between the absorbance of the reference dye—i.e., directly from the reservoir 16 and before the protein reaction—and the absorbance of the dye filtrate remaining after a reaction with a protein sample.

Figure 2:
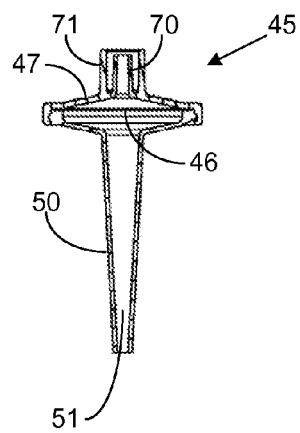
FIGS. 2, 3 and 4 are respective cross-sectional, perspective, and exploded cross-sectional views of the filter holder and filter media.
Figure 3:
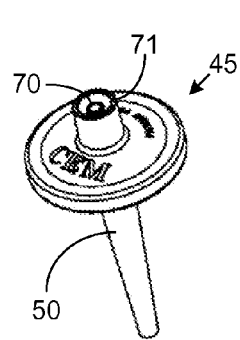
Figure 4:
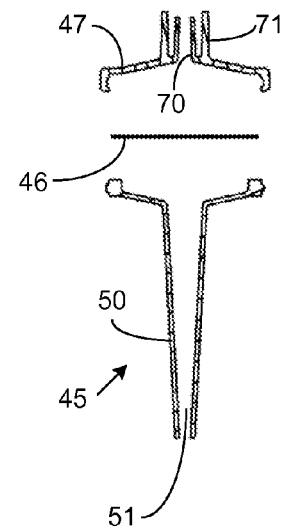

FIGS. 2-4 illustrate a filter holder 45 for use as just described and in accordance with the embodiments of the invention illustrated in FIGS. 7-13. The cross-sectional view of FIG. 2 illustrates that the filter holder 45 includes a substantially planar filter medium 46 maintained between an upper housing 47 and a lower housing 50. The housing portions 47 and 50 together define a filtrate passage 51 axially through the filter holder 45. The lower housing 50 defines a spout that depends from the filter medium 46. In use, the depending spout reached bottom portions of a sample cup 10 (FIGS. 5 and 6) when the filter medium 46 is positioned above the cup 10. As will be further understood with respect to FIGS. 7-13, because the depending spout reaches lower portions of the cup 10, it helps encourage liquid, rather than protein solids or the dye precipitate from clogging the filter medium 46. In an exemplary embodiment, the filter medium is a plastic scrim (for structural support) combined with glass fibers.

Figure 16:
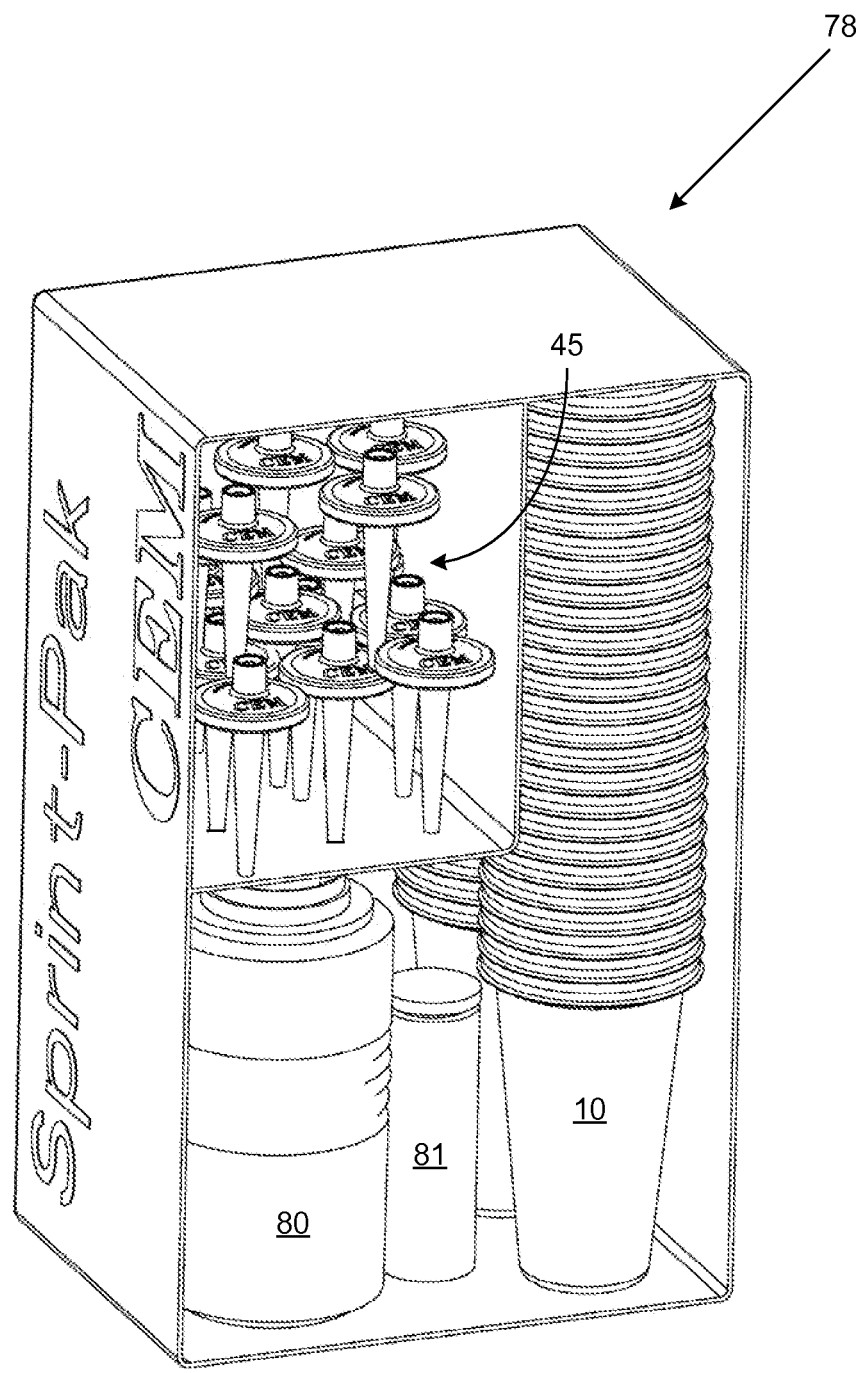
FIG. 16 is a perspective view of a protein analysis kit according to the present invention.

Thus, in another embodiment the invention is a kit that includes the sample cup 10 and the filter holder 45. In exemplary embodiments, and as illustrated in FIG. 16, the kit (broadly designated at 78) includes a plurality of cups 10 and holders 45 (e.g., 50 of each) along with a container 80 of dye binding solution and a container 81 of wash solution. The amount of dye binding and wash solutions provided in the kit 78 is sufficient to carry out a number of tests equivalent to the number of cups 10 and filter holders 45.

Figure 5:
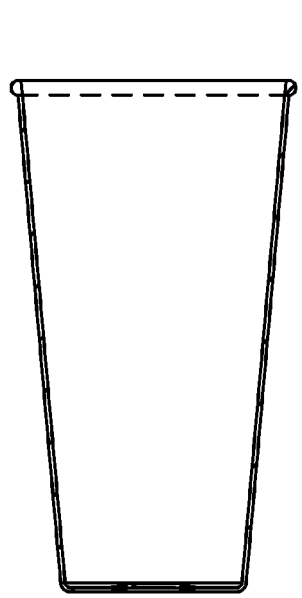
FIG. 5 is a cross-sectional view of a sample cup according to the present invention.
Figure 6:
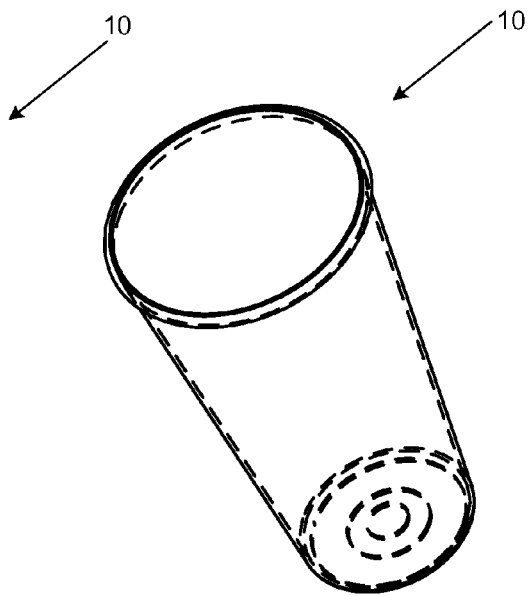
FIG. 6 is a perspective view of a sample cup according to the present invention.
Figure 7:
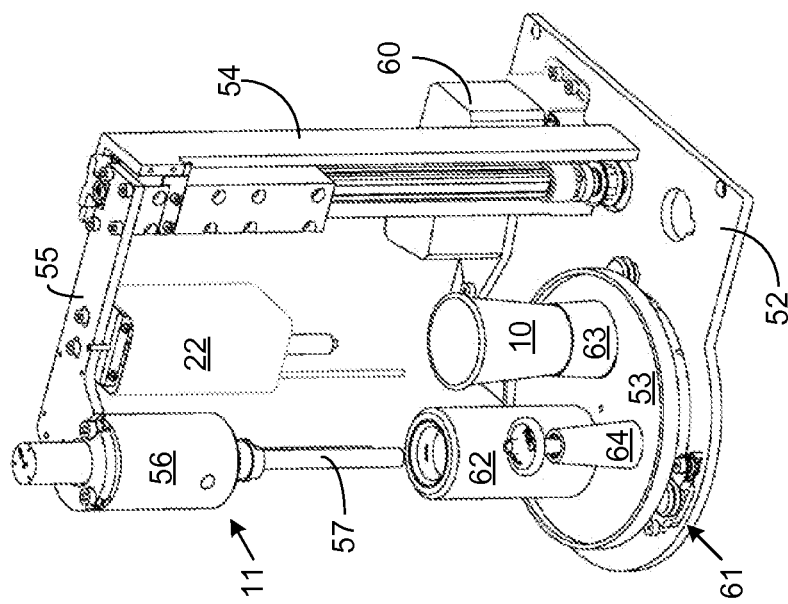
FIG. 7 is a perspective view of the turntable, homogenizer, and optical sampling components of the invention.
Figure 8:
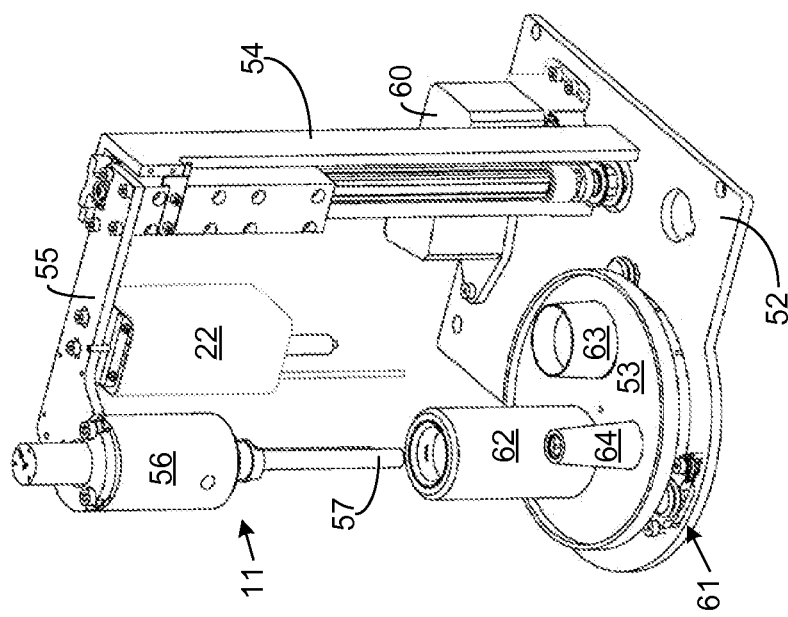
FIGS. 8-13 illustrate the same components as FIG. 7, but additionally illustrating the respective positions and movement of the sample cup, the filter, and the optical system during a protein analysis measurement.

FIGS. 5 and 6 illustrate a sample cup 10 (representing the same element as in the schematic view of FIG. 1) used in accordance with the embodiments illustrated in FIGS. 7 and 8. Both the filter 45 holder and the sample cup 10 can be formed of polymers making them easy to manufacture, light weight, low cost, and minimally waste generating, all of which makes them suitable for use as consumable items. Being consumable, the need to clean them between uses can be eliminated and the possibility that prior uses will contaminate the results of any given test can be eliminated.

FIGS. 7-14 illustrate one embodiment of a protein analyzer according to the present invention. Most of the features will be described with respect to FIGS. 7 and 8, and it will be understood that the same items appear in FIGS. 9-13 even if not specifically re-described.

FIGS. 7-13 specifically illustrate a series of stages (or steps) that together define one protein analysis cycle using this particular embodiment. FIG. 7 illustrates the first stage. In commercial embodiments the illustrated elements will typically be surrounded by housing, but FIGS. 7-13 avoid including extraneous items for purposes of clarity. Accordingly, FIG. 7 shows a platform 52 that supports a turntable 53 and a vertical translator 54. The vertical translator 54 includes a horizontal arm 55 that carries the homogenizer 11 and the colorimeter 22.

The homogenizer 11 includes a motor portion 56 and a blade shaft 57.

A motor 60 and related controls operate the vertical translator 54. Another motor and associated pulleys illustrated together at 61 drives the turntable 53.

The turntable 53 includes three stations: the wash station 62 shown as the vertically oriented open cylinder, a cup holder 63 and the filter rest 64.

FIG. 7 illustrates the turntable 53 in the home position before an operator places the cup 10 (and its sample) and the filter 45 in their respective holders.

FIG. 8 illustrates the same orientation as FIG. 7, but with the sample cup 10 in the sample cup holder 63 and the filter holder 45 in the filter rest 64. In bench top operation, an operator will typically position the cup 10 in the cup holder 63 and the filter holder 45 in the rest 64. This is exemplary, however, rather than limiting of the invention and these steps could be automated as well.

Figure 9:
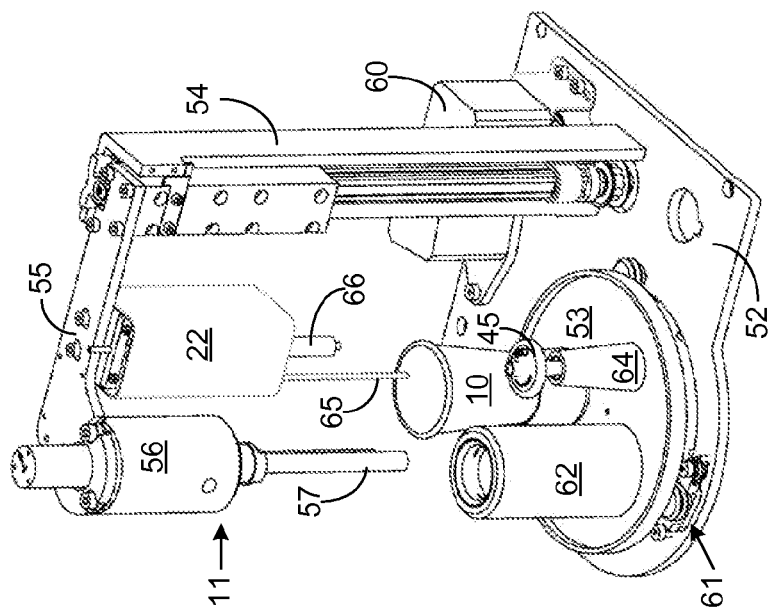

FIG. 9 illustrates the third stage of the operation in which the turntable has rotated to the position at which the binding dye is added to the sample cup. The dye is added through a dye addition tube 65 that in the illustrated embodiment is posited behind the colorimeter 22. In this position the sample cup 10 is under the dye addition tube 65. In one embodiment, the turntable 53 can also include means (not visible in FIG. 9) for individually rotating the cup holder 63 on the turntable 53 in order to rotate the cup 10 as the dye is being added. This additional rotation helps mix the sample and dye in the cup 10.

Figure 10:
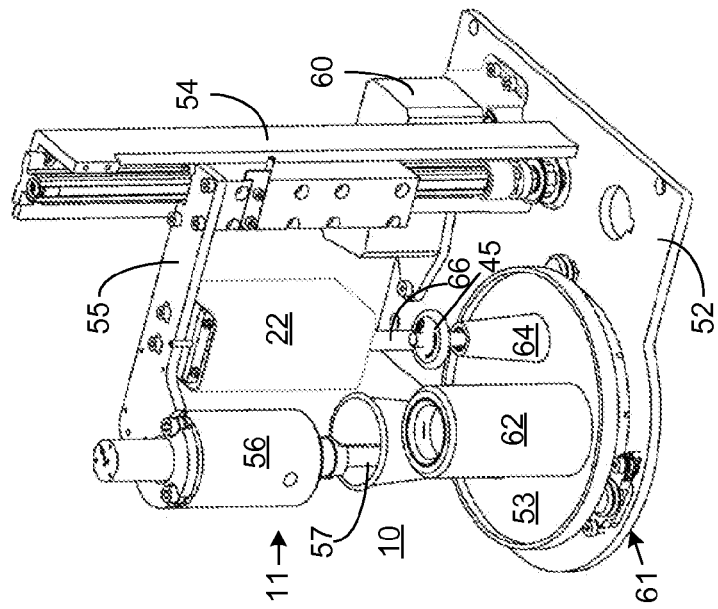

FIG. 10 illustrates the fourth stage of the process which can be referred to as the homogenization position. In this position, the cup 10 is positioned under the homogenizer 11 and its blade shaft 57. The filter 45 is in turn positioned under the colorimeter 22. FIG. 10 also shows that in this position the vertical translator 54 has lowered the position of the horizontal arm 55 to position the blade shaft 57 in the cup 10. At the same time, the optics tube 66 engages the top of the filter holder 45 to temporarily fix the filter holder 45 to the colorimeter. The sample is homogenized in this position.

Figure 11:
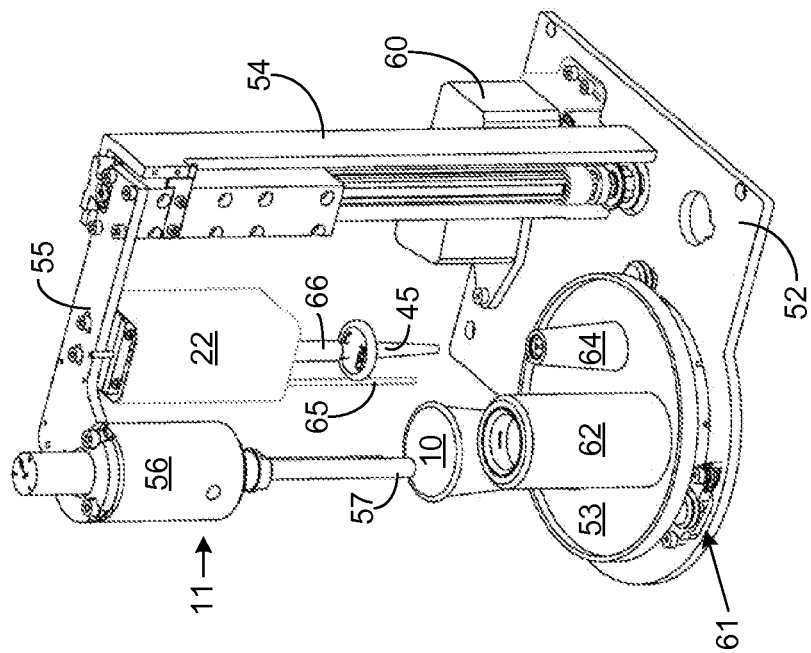

FIG. 11 shows the fifth stage in the process in which the vertical translator 54 has raised the colorimeter 22 and the homogenizer 11 so that the blade shaft 57 is above the cup 10 and the filter holder 45, still engaged to the optics tube 66, has likewise been raised above the filter rest 64.

Figure 12:
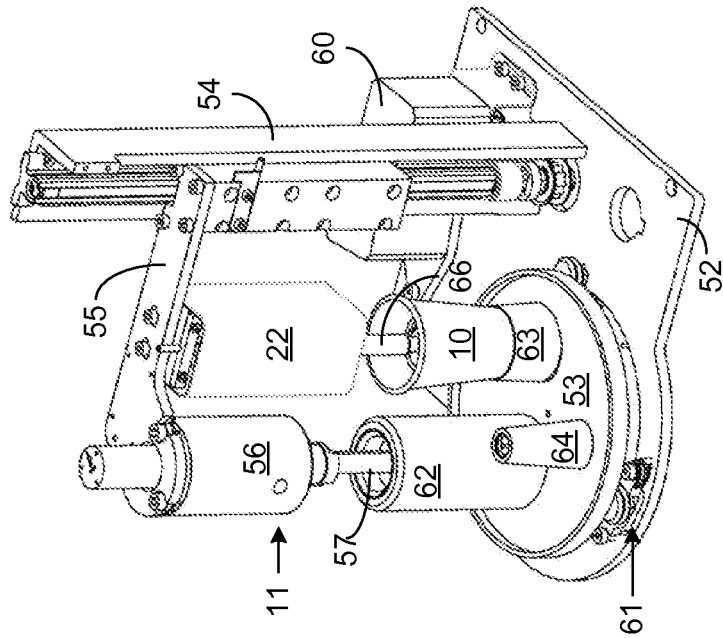

FIG. 12 shows the sixth stage in the process which represents the sampling position. The turntable 53 has rotated clockwise (with respect to FIGS. 11 and 12) to position the cup 10 with its sample underneath the colorimeter 22 and to align the homogenizer 11 with the cleaning station 62. When, as illustrated in FIG. 12, the vertical translator 54 lowers the horizontal arm 55, the blade shaft 57 is likewise lowered into the cleaning station 62 and the filter holder 45 is lowered into the sample cup 10. In this position, the sample pump draws the sample up into and through the filter holder 45. The filter media (e.g., 46 in FIGS. 2 and 4) allows only filtrate to reach the colorimeter 22. The colorimeter 22 then takes the absorbance reading in an otherwise well understood manner. As set forth in the description of FIG. 1, in this step deionized water or another solution can be added to the cleaning station 62 to clean the homogenizer 11, and in particular the blade shaft 57. In this embodiment the pump (not shown) is positioned upstream of the colorimeter 22 and in fluid communication with the supply of de-ionized water or cleaning solution (e.g. the wash reservoir 42 in FIG. 1). This arrangement permits the pump to draw samples into the colorimeter while handling only deionized water. In this embodiment, the pump can also run in the opposite direction to flush the sample from the colorimeter 22.

FIG. 12 also illustrates the advantage of the filter holder 45. In the sampling position illustrated in FIG. 12, the filter holder 45 is inserted into the sample cup 10. Although not illustrated in FIG. 12, those familiar with the step of homogenizing a dye-binding solution with a solid protein (e.g., meat) recognize that the homogenization and dye reaction tend to generate a significant amount of foam along with the dye-protein precipitate and the remaining solids in the meat sample.

Because the filter holder 45 includes the spout 50 that complements the size and shape of the cup 10 (FIGS. 15 and 16), the sample holder 45 tends to avoid drawing excess solids to the filter. As a result, the filter holder and cup arrangement encourages a freer flow of liquid to the filter and a correspondingly better flow of filtrate from the filter into the colorimeter.

Figure 13:
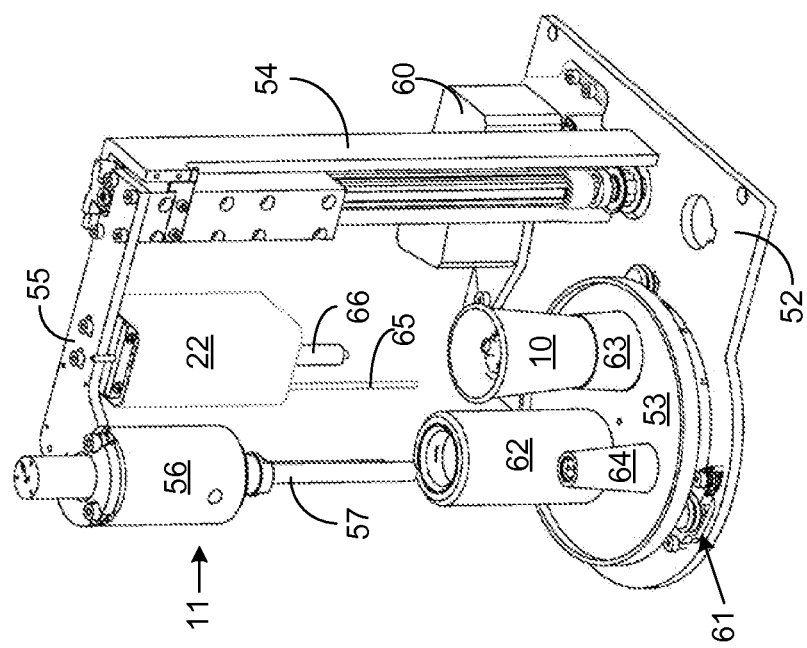

In one aspect, this arrangement of the cup 10 and filter holder 45 eliminates the need for the pre-homogenizing dilution step with methanol and citric acid that is characteristic of certain conventional dye-binding techniques. In turn, eliminating the dilution step eliminates any potential error introduced with the dilution step and also facilitates the automation of the process using the instrument FIG. 13 illustrates the seventh and completion stage of the process as carried out with this embodiment. The optics tube 66 ejects the filter holder 45 into the cup 10 and the optics are flushed with an appropriate liquid that can collect in the cup 10. Thus, at the end of this stage, and when the vertical translator 54 again raises the horizontal arm 55, the original sample, the used filter holder 45, and the rinse from the colorimeter 22 are all in the cup 10. These items can be easily disposed of together. Removing the used sample cup 10, the used filter holder 45 and the waste solutions returns the instrument to the first stage orientation and ready for the next sample as originally illustrated in FIG. 7.

In this regard, FIGS. 2-4 illustrate an exemplary embodiment in which the upper housing 47 of the filter holder 45 includes a male seal 70 and an ejector sheath 71. This combination cooperates with the optics tube 66 to facilitate the engagement with, and the disengagement of, the optics tube 66 and the filter holder 45.

Figure 15:
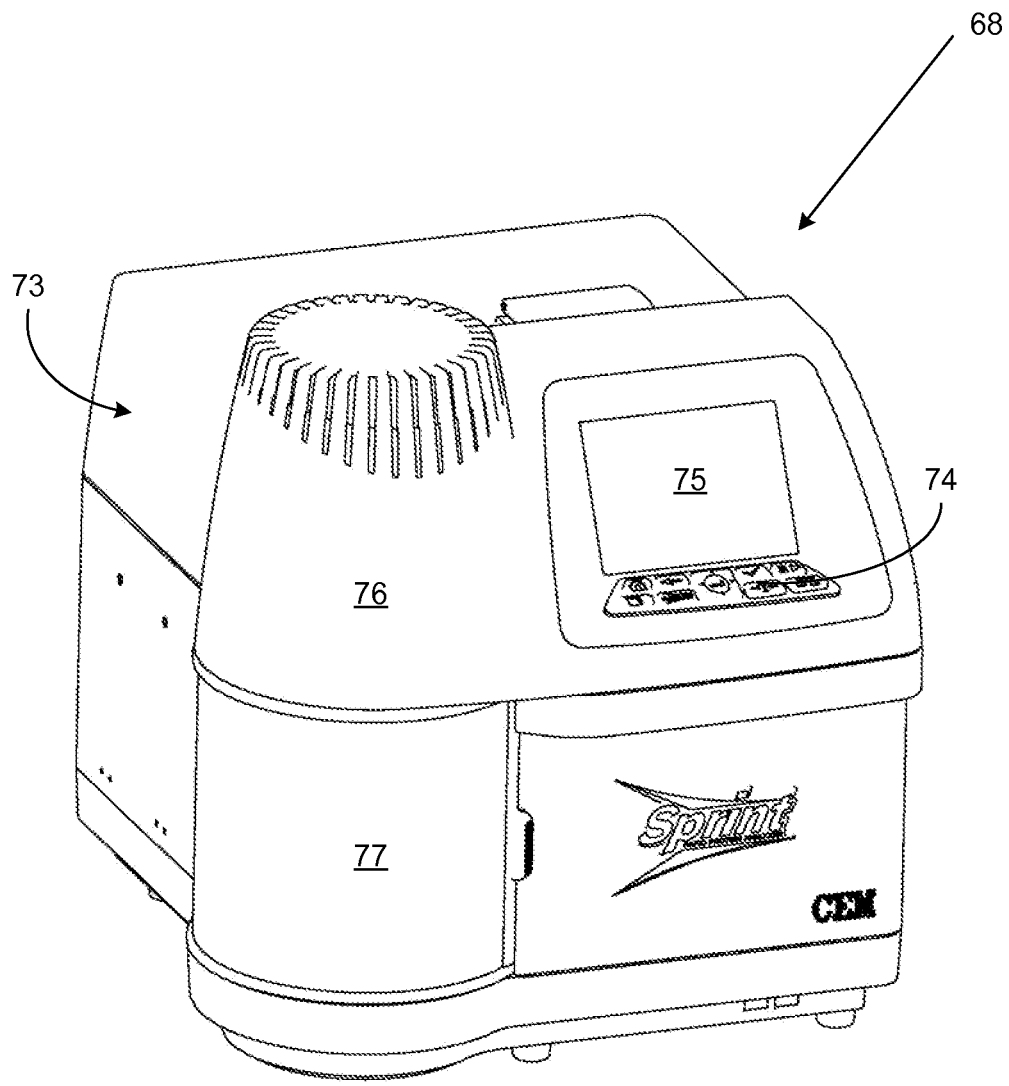
FIG. 15 is a perspective view of the analyzer according to the invention in the context of its housing.

FIG. 15 is a perspective view of the instrument broadly designated at 68 in the context of its housing broadly designated at 73. A keyboard or analogous control panel 74 can be used to provide relevant instructions to the device and operates in combination with a display 75. As noted earlier, the nature of individual control panels, processors, controllers, and displays is generally well understood in this art and will not be described in detail.

In the embodiment illustrated in FIG. 15, the housing 73 includes a generally cylindrical portion 76 which in this embodiment represents the position of the turntable 53 and the associated elements of the instrument that are illustrated in FIGS. 7 through 13. The cylindrical housing portion 76 includes a door 77 that can be opened and closed to position new samples on the turntable 53 or remove analyzed samples from the turntable 53.

In another aspect, the invention is a dye binding method for protein analysis. In this aspect, the invention comprises preparing an initial reference dye solution of unknown concentration from an initial reference dye concentrate. Reference dye concentrates of known concentration are available in the art, but as described further herein, the method and instrument of the invention can eliminate some of the measuring steps that conventional methods require. Typically, a reference dye solution can be prepared by diluting a reference dye concentrate with water, and potentially items such as a weak acid (e.g., acetic) to adjust pH or an alcohol (e.g., ethanol) to reduce foaming.

The method next includes the step of creating an electronic (e.g., digital or analog) signal based upon the absorbance of the initial reference dye solution. The absorbance is used herein in its conventional sense to refer to a Beer's Law analysis as discussed earlier with respect to the instrument.

In the following step, the method includes creating an electronic signal based upon the absorbance of a dye filtrate solution prepared from the initial reference dye solution and an initial protein sample. The absorbance signals from the reference dye solution and the dyed filtrate solution are respectively sent to a processor that compares the respective absorbances and calculates the protein content of the protein sample based upon the differences between the absorbances.

The method next includes the step of creating an electronic signal based upon the absorbance of a successive dye filtrate solution prepared from the reference dye solution and a successive protein sample.

The absorbance signal from the successive sample dye filtrate solution is also sent to the processor to calculate the protein content of the successive sample based upon the difference between the absorbance of the initial reference dye solution and the absorbance of the successive dye filtrate solution.

The method can further comprise the step of weighing a protein sample and mixing the sample with the initial dye reference solution prior to creating the electronic signal based upon the dye filtrate solution. In turn, the step of weighing the protein sample can comprise adding the sample to a tared sample cup and weighing the cup and the sample.

The method can further comprise the step of homogenizing the sample after the step of weighing the sample. This in turn particularly distinguishes the method and instrument of the invention from prior techniques in which the homogenization of the sample is typically carried out prior to the step of weighing the material. The step of homogenizing the sample can be selected of the group consisting of grinding, pulverizing, blending, milling, and combinations thereof.

After the sample has been homogenized, the method can comprise mixing the reference dye solution with the homogenized sample by physically agitating the dye solution and the sample. The method includes filtering the mixture of the initial reference dye solution and the initial protein sample prior to the step of creating the electronic signal based upon the absorbance of the filtrate. In the same manner, the method includes the steps of filtering a mixture of a successive reference dye solution and a successive protein sample prior to the step of creating the electronic signal based upon the absorbance of the filtrate.

Although the term "filtrate" nominally refers to a solution from which solids have been filtered, in the context of the present invention it can be used to describe any post-reaction dye solution from which solids have been separated. For example, centrifuging the solids from the protein-dye mixture will produce an appropriate filtrate.

As a particular advantage, the method includes repeating the protein-dye analysis to produce successive dye filtrate solutions until the initial reference dye solution is exhausted. A successive reference dye solution of unknown concentration is then prepared from a reference dye concentrate. The remaining analysis steps are then repeated for successive dye filtrate solutions formed from successive reactions between the successive reference dye solution and successive protein samples.

Once the initial reference by solution is exhausted, the successive reference dye solution can be prepared from the initial reference dye concentrate or from a different dye concentrate, because the method and related instrument provide the opportunity to recalibrate based on every reference dye solution.

In another aspect, the invention comprises a method of calibrating a colorimeter for protein analysis and analyzing a plurality of protein samples. In this aspect the method comprises preparing an initial reference dye solution of unknown concentration from an initial reference dye concentrate and an approximate amount of liquid. As in the other embodiments, the liquid is primarily de-ionized water but can also include items such as acetic acid or ethanol.

The initial reference dye solution—without reacting with anything—is forwarded to a colorimeter where the absorbency of the initial reference dye solution is measured in a Beer's Law context. Thereafter, an initial dye filtrate solution that has been prepared from the reaction of the initial reference dye solution and a protein sample is forwarded to the colorimeter and the colorimeter measures the absorbency of the initial dye filtrate solution.

The absorbance results from the initial dye filtrate solution and the initial reference dye solution are sent to a processor that compares the respective absorbances and calculates the protein content of the sample based upon the difference between the absorbances.

Then, a successive dye filtrate solution—from a successive dye-protein reaction—is sent to the colorimeter and the absorbency of the successive dye filtrate solution is measured. The absorbance results from the successive dye filtrate solution are sent to the processor to calculate the protein content of the successive sample based upon the difference between the absorbance of the initial reference dye solution and the absorbance of the successive dye filtrate solution.

In this method, the step of forwarding the sample dye solution can further comprise the steps of mixing a protein sample with a portion of the initial reference dye solution, then filtering the protein-dye precipitate generated when the protein sample reacts with the initial reference dye solution, and then forwarding the filtrate to the colorimeter.

As in the other embodiments, the protein sample is typically homogenized before being mixed with the initial reference dye solution.

The method can further comprise repeating the step of forwarding successive dye filtrate solutions to the colorimeter until the initial reference dye solution prepared from the reference dye concentrate is exhausted. Then, a successive reference dye solution can be prepared by mixing a reference dye concentrate with a successive approximate amount of liquid to produce a successive working dye solution of unknown concentration.

The method can further comprise repeating the steps of forwarding the reference dye solution, forwarding the dye filtrate solution, sending the absorbance results, forwarding the successive dye filtrate solutions, and sending the successive absorption results, all following the step of mixing the successive portion of liquid with reference dye concentrate.

As in the other embodiments, the successive reference dye solution can be prepared from the initial reference dye concentrate or from a different reference dye concentrate.

Figure 14:
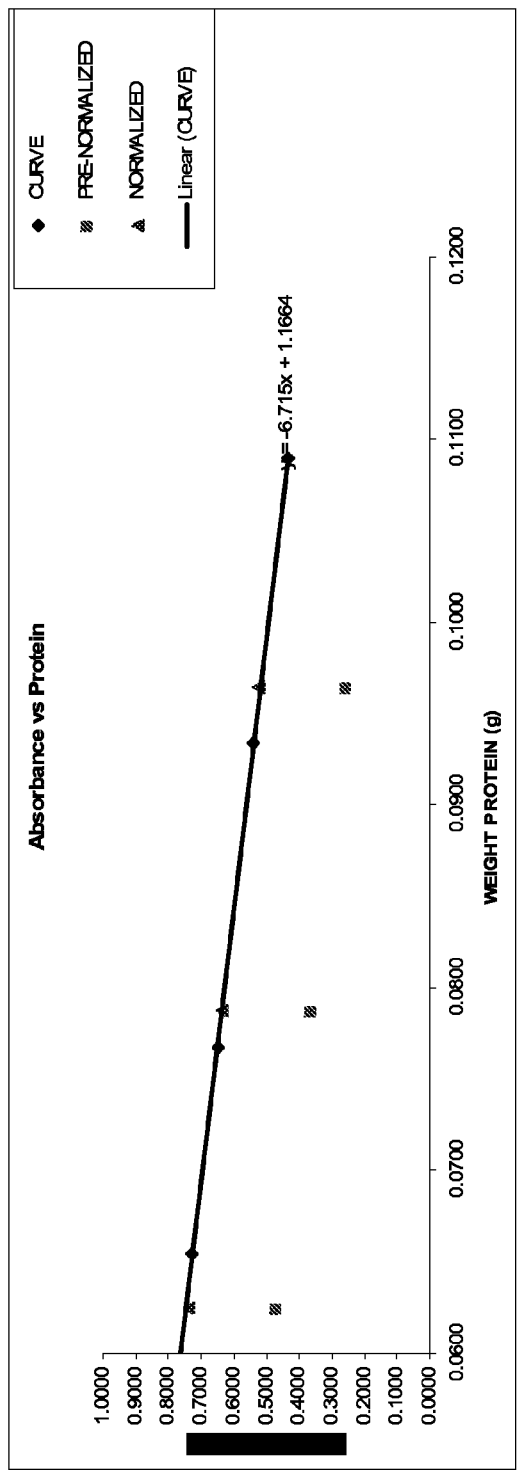
FIG. 14 is an exemplary normalized plot of absorbance versus protein content for measurements according to the present invention.

FIG. 14 illustrates the manner in which the protein content of general categories of samples can be normalized so that the instrument provides consistent results as the reference dye solution is used and then replenished. FIG. 14 also relates to Tables 1-4.

The purpose of normalization is to standardize the instrument so that different initial dye concentrations produce consistent protein content results. As noted previously, the dye binding technique depends fundamentally upon the difference in absorbance (color density) between the dye before it reacts with protein and after it reacts with protein. If the starting concentration (color) of the dye solution is increased (or decreased), then the color intensity after reaction will be correspondingly greater (or less) for all protein samples tested with that dye solution.

Stated in yet another fashion, a more concentrated starting dye solution will produce a more concentrated solution even after reaction with a certain amount of protein. In the same manner, a less concentrated starting dye solution will produce a less concentrated solution after reaction with a certain amount of protein. Thus, an identical protein sample will give different colorimeter results based on different starting dye concentrations. Accordingly, the normalization step compensates for the difference in the initial dye solutions and produces a consistent output from the instrument.

Tables 1-4 illustrate one method for normalizing the results as between two different initial dye solutions.

Table 1 presents data from a first dye solution arbitrarily designated as "A." The "A" dye solution is placed in the colorimeter to obtain its absorbance reading (28.56 in this example). A blank sample of de-ionized water is then immediately placed in the same colorimeter to obtain its transmission (443.60). The absorbance (1.191) of the "A" initial dye solution is then calculated according to the formula $$\text{Absorbance} = \log(\text{dye transmission/blank transmission}).$$

Table 2 gives the results for four (4) samples of turkey paste using the "A" initial dye solution. In order to create a baseline for the analysis, the turkey paste was first tested using the Kjeldahl method, which indicated a protein content of 31.23 percent by weight.

Four respective samples of this turkey paste were then tested using the instrument and method of the invention ("Reading"). Each sample reading was followed immediately by a reading of deionized water ("Blank"). The absorbance was calculated on this basis. The results were then plotted using a least squares analysis to form the straight line illustrated in FIG. 14. The theoretical protein percent was then taken from the least squares line ("Theoretical Protein (%)") and the comparisons to the Kjeldahl results ("Error") were calculated for each sample.

Table 3 represents a second initial dye solution designated as "B" which was purposefully made to a different concentration than the "A" initial dye solution. Its transmission, the transmission of a deionized water blank, and the absorbance of the "B" solution were appropriately calculated.

The difference between the absorbance of the "A" initial dye solution (1.191) and the absorbance of the "B" initial dye solution (0.923) represents the extent to which results using the "B" initial dye solution must be normalized to give results consistent with the "A" initial dye solution.

Table 4 shows these results for three more samples of the same turkey paste. The raw results using the "B" dye solution are plotted as the small squares in the lower portion of FIG. 14. When the difference between the initial absorbances of the "A" and "B" solutions are added to the "B" data points, the "B" data points fall as the triangles in FIG. 14. Because the triangles now fall along the least squares line created from the "A" solution, the results using the "B" solution can be compared directly to the results of the "A" solution.

This normalization step can be carried out in the same manner for third and succeeding concentrations of the initial dye solution thus providing the instrument with the capability to provide consistent protein content results independent of normal variations in the concentration of initial dye solutions.

Turkey Paste Normalization Trial

TABLE 1

| Tank | Reading | Blank | $A_{TANK}$ |
|---|---|---|---|
| A | 28.56 | 443.60 | 1.191 |

TABLE 2

| Sample | Weight (g) | wt protein | Reading | Blank | Abs | Theoretical Protein (%) | Error (%) |
|---|---|---|---|---|---|---|---|
| 1 | 0.2096 | 0.0655 | 83.19 | 445.2 | 0.7285 | 31.11 | 0.12 |
| 2 | 0.2458 | 0.0768 | 100 | 444.9 | 0.6483 | 31.39 | 0.16 |
| 3 | 0.2992 | 0.0934 | 128.2 | 444.6 | 0.5401 | 31.17 | 0.06 |
| 4 | 0.3491 | 0.1090 | 163.4 | 444.2 | 0.4343 | 31.23 | 0.00 |

TABLE 3

| Tank | Reading | Blank | $A_{TANK}$ |
|---|---|---|---|
| B | 52.78 | 442.30 | 0.923 |

TABLE 4

| | | | | | NORMALIZED A | Normalized Theo (%) |
|---|---|---|---|---|---|---|
| 1 | 0.2521 | 0.0787 | 190.5 | 442.3 | 0.3658 | 0.634 | 31.46 |
| 2 | 0.2002 | 0.0625 | 150 | 442.2 | 0.4695 | 0.738 | 31.90 |
| 3 | 0.309 | 0.0965 | 245.3 | 441.9 | 0.2556 | 0.524 | 30.98 |

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A dye binding method for protein analysis consisting essentially of:
    preparing an initial reference dye solution of unknown concentration by mixing an initial reference dye concentrate with water;
    creating an electronic signal based upon the absorbance of the initial reference dye solution;
    thereafter, creating an electronic signal based upon the absorbance of a dye filtrate solution prepared from a weighed initial protein sample homogenized in the initial reference dye solution and filtered from the homogenate;
    sending the absorbance signals from the reference dye solution and the dye filtrate solution to a processor that compares the respective absorbances and calculates the protein content of the weighed protein sample based upon the difference between the absorbances;
    creating an electronic signal based upon the absorbance of a successive dye filtrate solution prepared from a successive weighed protein sample homogenized in the initial reference dye solution and filtered from the homogenate; and
    sending the absorbance signal from the successive sample dye filtrate solution to the processor to calculate the protein content of the successive sample based upon the difference between the absorbance of the initial reference dye solution and the absorbance of the successive dye filtrate solution.

2. A protein analysis method according to claim 1 comprising weighing the protein sample by adding the sample to a tared sample cup and weighing the cup and the sample.

3. A protein analysis method according to claim 1 wherein the step of homogenizing the sample is selected from the group consisting of grinding the sample, pulverizing the sample, blending the sample, milling the sample, and combinations thereof.

4. A protein analysis method according to claim 1 further comprising separating a mixture of the initial reference dye solution and the initial protein sample prior to the step of creating the electronic signal based upon the absorbance of the filtrate.

5. A protein analysis method according to claim 1 comprising:
    repeating the analysis of successive dye filtrate solutions until the initial reference dye solution is exhausted;
    thereafter preparing a successive reference dye solution of unknown concentration from a reference dye concentrate; and
    repeating the remaining steps of claim 1 for further successive dye filtrate solutions formed from successive reactions between the successive reference dye solution and successive protein samples.

6. A protein analysis method according to claim 1 comprising preparing the successive reference dye solution from the initial dye concentrate.

7. A protein analysis method according to claim 1 comprising preparing the successive reference dye solution from a different dye concentrate.

8. A protein analysis method according to claim 1 further comprising filtering the initial reference dye solution prior to the step of creating the electronic signal based upon the absorbance of the initial reference dye solution.

9. A method of calibrating a colorimeter for protein analysis and analyzing a plurality of protein samples, the method consisting essentially of:
    preparing an initial reference dye solution of unknown concentration by mixing an initial reference dye concentrate and an approximate amount of water;
    forwarding the initial reference dye solution to a colorimeter and measuring the absorbency of the reference dye solution;
    thereafter, forwarding an initial dye filtrate solution prepared from the reaction of the initial reference dye solution homogenized with a weighed protein sample to the colorimeter and measuring the absorbency of the initial dye filtrate solution;
    sending the absorbance results from the initial dye filtrate solution and the initial reference dye solution to a processor that compares the respective absorbance and calculates the protein content of the weighed sample based upon the difference between the absorbances;
    forwarding a successive dye filtrate solution to the colorimeter and measuring the absorbency of the successive dye filtrate solution; and
    sending the absorbance results from the successive dye filtrate solution to the processor to calculate the protein content of the successive sample based upon the difference between the absorbance of the initial reference dye solution and the absorbance of the successive dye filtrate solution.

10. A protein analysis method according to claim 9 wherein the step of forwarding the sample dye solution further comprises the steps of:
    mixing a protein sample with a portion of the initial reference dye solution;
    filtering the protein-dye precipitate generated when the protein sample reacts with the initial reference dye solution; and
    forwarding the filtrate to the colorimeter.

11. A protein analysis method according to claim 9 comprising repeating the step of forwarding successive dye filtrate solutions to the colorimeter until the solution prepared from the reference dye concentrate is exhausted.

12. A protein analysis method according to claim 11 comprising the step of mixing a successive reference dye solution from a reference dye concentrate with a successive approximate amount of water to produce a successive working dye solution of unknown concentration.

13. A protein analysis method according to claim 12 further comprising carrying out the steps of:
   forwarding the reference dye solution, forwarding the dye filtrate solution, sending the absorbance results, forwarding a successive dye filtrate solution, and sending the successive absorbance results;
   all following the step of mixing the successive portion of water with reference dye concentrate.

14. A protein analysis method according to claim 12 comprising mixing the successive reference dye solution from the initial reference dye concentrate.

15. A protein analysis method according to claim 12 comprising mixing the successive reference dye solution from a different concentrate from the initial reference dye concentrate.

\* \* \* \* \*